(12) United States Patent
Rahman (10) Patent No.: US 6,361,317 B1
(45) Date of Patent: Mar. 26, 2002

(54) MOLDED, REINFORCED HANDLE

(75) Inventor: Anisur Mithu Rahman, Gurnee, IL (US)

(73) Assignee: Hu-Friedy Mfg. Co., Inc., Chicago, IL (US)

( * ) Notice: Subject to any disclaimer, the term of this patent is extended or adjusted under 35 U.S.C. 154(b) by 0 days.

(21) Appl. No.: 09/602,433

(22) Filed: Jun. 23, 2000

(51) Int. Cl.[7] .................................................. A61C 3/00
(52) U.S. Cl. ........................................ 433/141; 81/489
(58) Field of Search ................... 433/141, 143, 433/147, 142, 144, 146; 81/489; 16/DIG. 19, DIG. 18, 421, 430, 431, 436, 422, 110.1; D8/303, 300, 107

(56) References Cited

U.S. PATENT DOCUMENTS

| | | |
|---|---|---|
| 2,818,647 A | 1/1958 | Berliner |
| 4,060,897 A | 12/1977 | Greenstein |
| D249,062 S * | 8/1978 | Crafoord et al. ............. D24/10 |
| 4,759,713 A | 7/1988 | Heiss et al. .................. 433/141 |
| 4,795,344 A | 1/1989 | Brewer, Jr. .................. 433/143 |
| 4,882,867 A | 11/1989 | Linden ......................... 40/625 |
| 5,100,321 A * | 3/1992 | Coss et al. ................... 433/118 |
| 5,501,597 A | 3/1996 | Wilson ........................ 433/141 |
| 5,578,050 A * | 11/1996 | Webb .......................... 606/167 |
| D394,902 S | 6/1998 | Herbst et al. ............... D24/154 |
| 5,816,806 A | 10/1998 | Herbst et al. ............... 433/141 |
| 5,893,713 A * | 4/1999 | Garman et al. ................ 433/32 |
| 6,042,378 A * | 3/2000 | Fischer et al. .............. 433/141 |
| 6,109,918 A * | 8/2000 | Hammond et al. .......... 433/141 |
| 6,261,099 B1 * | 7/2001 | Senia et al. .................. 433/224 |

OTHER PUBLICATIONS

American Eagle Instruments, Inc., We'e Got "The Handle" on Carpal Tunnel, Published before Jul. 31, 1996.
Hu–Friedy Dutch Catalog, Published before Jul. 31, 1996.

* cited by examiner

Primary Examiner—John J. Wilson
Assistant Examiner—Melba Bumgarner
(74) Attorney, Agent, or Firm—Rockey, Milnamow & Katz, Ltd.

(57) ABSTRACT

A dental instrument includes a plastic molded handle body which is reinforced by a metallic tube through a center of the body. Tool parts are adhesively secured into opposing open ends of the reinforcing tube. During assembly, a quantity of adhesive is pre-positioned into the open ends. The tool parts include respective base parts that provide glue traps for capturing a quantity of the pre-positioned adhesive and ensuring adequate adhesive contact between the tool part and the tool. The molded body has surface contours which are molded by a mold having a single parting plane.

31 Claims, 7 Drawing Sheets

MOLDED, REINFORCED HANDLE

FIELD OF THE INVENTION

The invention pertains to dental instruments. More particularly, the invention pertains to dental instruments which have reinforced, molded handles.

BACKGROUND OF THE INVENTION

Hand held dental instruments include an elongated shaft for gripping and manipulation by the dental practitioner and a tool or point located at one or both ends of the shaft. The tool or point is typically a stainless steel or other metallic material. The shaft is typically a stainless steel shaft, or a molded plastic shaft, or a molded plastic shaft having a central metal tube for reinforcement.

The tools or points can be inserted into metallic cones having receiving sockets for receiving a base of the tool. The cones can be brazed or welded to metal handles or metal reinforcing tubes. Alternatively, they can be insert molded or adhesively secured to a plastic handle. Examples of handle constructions are disclosed in U.S. Pat. Nos. 5,816,806; 5,501,597 and 4,882,867.

While the dental instruments having the metal shaft, or the metal tube reinforced plastic shaft, offer strength advantages, the techniques used to attach the tool parts are relative costly. The present inventor has recognized that it would be advantageous to provide a molded plastic handle with a metal reinforcing tube for a dental instrument, which handle carries one or more tool parts, wherein the tool parts can be effectively and securely attached to the handle.

SUMMARY OF THE INVENTION

A dental instrument includes a plastic elongated body having an elongated, metal, reinforcement extending through the body. The reinforcement includes at least one, and preferably two, hollow ends.

One, and preferably two working members, each of which has an affixing stem and an attached functional portion, are attached to the reinforcement. Particularly, the respective stems slide into the hollow ends and are adhesively attached to the reinforcement.

According to the preferred embodiments of the invention, the reinforcement comprises a hollow tube or rod. Each stem includes at least one glue trap.

During assembly, glue is applied in the hollow end of the reinforcement and the stem glue trap "captures" the glue as it is press fit into the reinforcement. Alternatively, the glue can be applied to the glue trap and the stem is press fit into the respective hollow end of the reinforcement.

According to the preferred embodiments, the working member comprises a tool having a tapered external surface which terminates in a blocking shoulder. When the stem is press fit into the hollow end of the reinforcement, the shoulder abuts the end of the reinforcement.

The plastic body of the handle can have a molded, contoured or knurled surface for assisting with gripping manipulation of the instrument by a dental practitioner. This is particularly important considering that the practitioner may be wearing surgical gloves which can become slippery with a patient's saliva. The contoured surfaces are also preferably sufficiently "rounded" or "dulled" to prevent the possibility of cutting a surgical or latex glove.

Adjacent to each tool at the ends of the handle, the plastic body is tapered toward the functional portion to provide a gripping and manipulation surface for the practitioner. Annular grooves are provided on these tapered ends to increase traction.

The molded contoured surfaces can be manufactured in a mold having only a single parting plane. This is accomplished by providing a contoured surface having raised elements over substantially the entire circumferential surface of the contoured regions, except that at the sides of the body the contours are circumferentially smooth, i.e., having no undercuts or axial cuts. This configuration permits the mold halves to be parted and separated along the single plane so the body can be removed from the mold.

Numerous other advantages and features of the present invention will become readily apparent from the following detailed description of the invention and the embodiments thereof, from the claims and from the accompanying drawings.

DETAILED DESCRIPTION OF THE PREFERRED EMBODIMENTS

While this invention is susceptible of embodiment in many different forms, there are shown in the drawing and will be described herein in detail specific embodiments thereof with the understanding that the present disclosure is to be considered as an exemplification of the principles of the invention and is not intended to limit the invention to the specific embodiments illustrated.

Figures 1, 2:
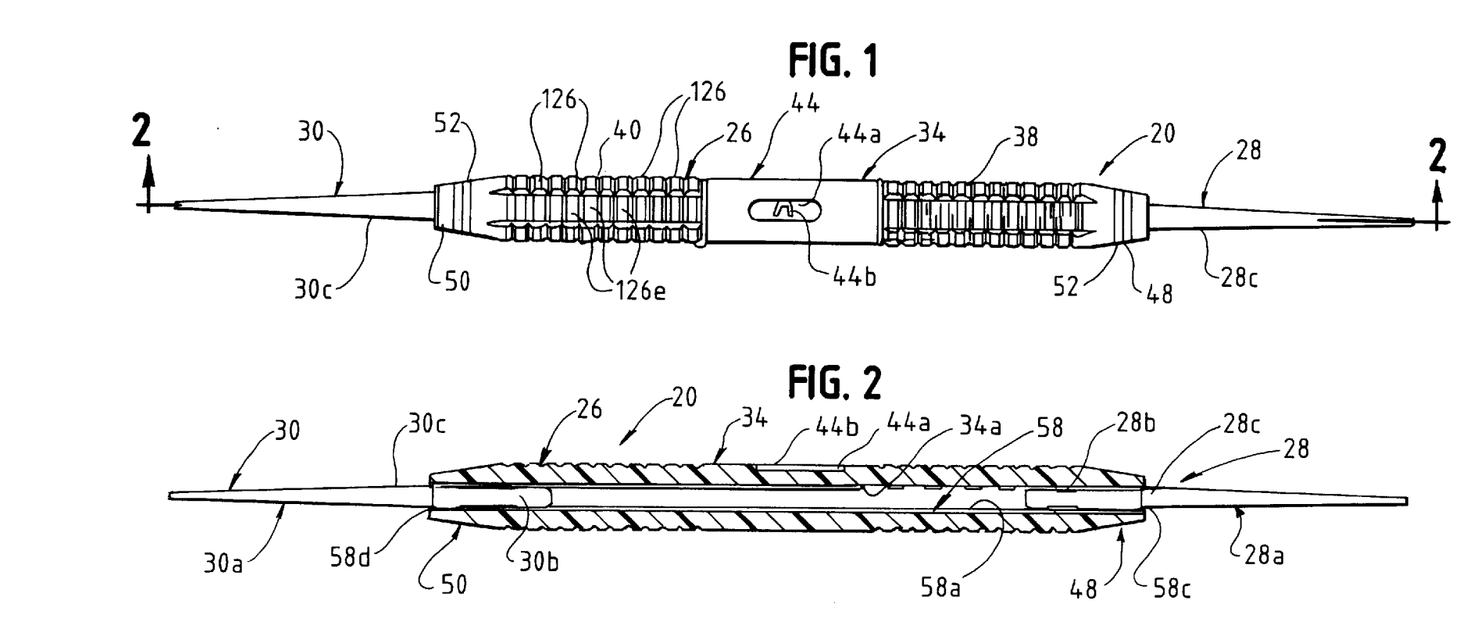
FIG. 1 is an elevational view of a dental instrument according to the invention.
FIG. 2 is a sectional view taken generally along line 2—2 of FIG. 1.

FIG. 1 illustrates a dental instrument 20 having a handle portion 26 and tools 28, 30 extending from opposite respective ends of the handle portion 26.

The handle portion 26 includes a molded plastic resin body 34 having contoured or knurled regions 38, 40 and a substantially smooth central region 44. The central region 44 can have a recess 44a for surrounding a molded trademark or other display 44a with the body 34. For illustrative purposes, the raised letter "A" is displayed.

Adjacent to each tool 28,30 is a tapered end region 48, 50 respectively. The tapered end regions include annular grooves 52 which increase gripping traction of a user's fingers.

The back side view of the instrument shown in FIG. 1 would be substantially identical. As described below, the contoured regions 38, 40 have substantially square molded protrusions 126 within top and bottom regions and elongated rectangles 126e within opposite side regions.

FIG. 2 illustrates that the body 34 has a central bore 34a. A metal reinforcing tube 58 is held within the bore 34a. The tube is preferably composed of stainless steel.

The metal tube 58 serves to strengthen the handle portion, especially for bending loads. The tube 58 can be captured within the bore 34a, or can be secured thereto by insert molding, adhesive or other technique.

The tools 28, 30 include working or functional portions 28a, 30a and base portions or attaching stems 28b, 30b. The base portions 28b, 30b are secured to an inside surface 58a of the tube 58 as described below.

Figure 5:
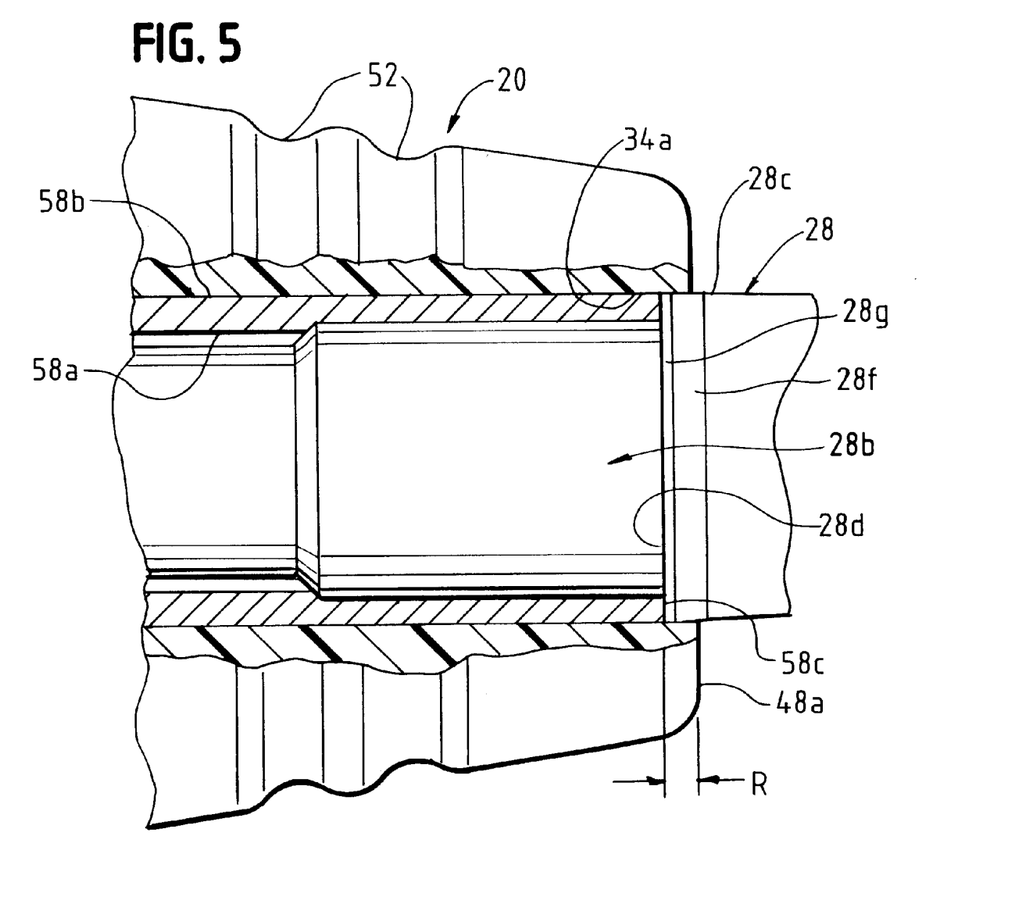
FIG. 5 is an enlarged fragmentary sectional view taken from FIG. 4.

The working portions 28a, 30a have tapered surfaces 28c, 30c adjacent the respective base portions 28b, 30b, which terminate in blocking shoulders 28d, 30d respectively (shown in FIG. 5). The shoulders are pressed against respective ends 58c, 58d of the tube 58.

Figure 3:
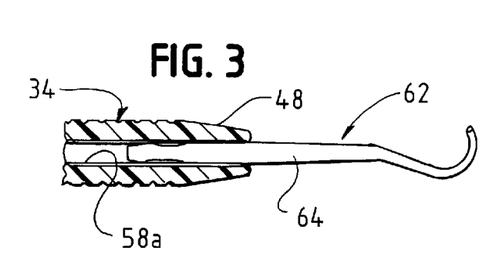
FIG. 3 is a fragmentary sectional view of an alternate embodiment dental instrument.

Although the working portions 28a, 30a are shown as substantially straight points or shafts, any type of tool or shape of tool is encompassed by the invention. For example, FIG. 3 illustrates a hook-shaped tool 62 mounted to a body 34. The tool 62 illustrated has a cylindrical shoulder 64, but could alternatively have a smooth, tapered surface such as shown for the tools 28, 30 in FIGS. 1 and 2.

Figure 4:
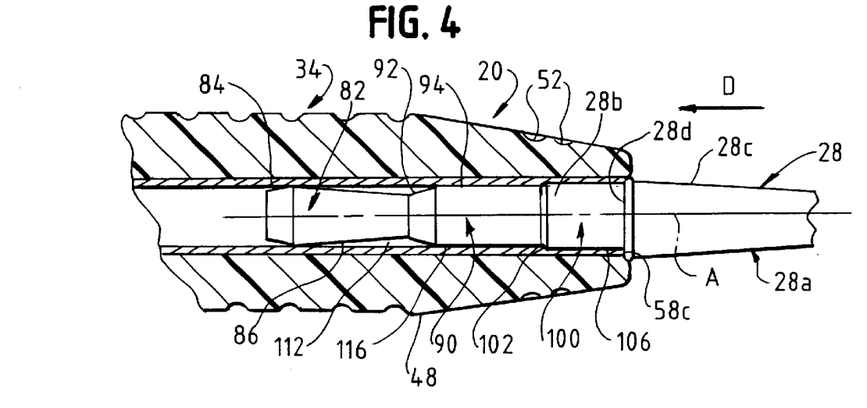
FIG. 4 is an enlarged fragmentary sectional view taken from FIG. 2.
Figure 4A:
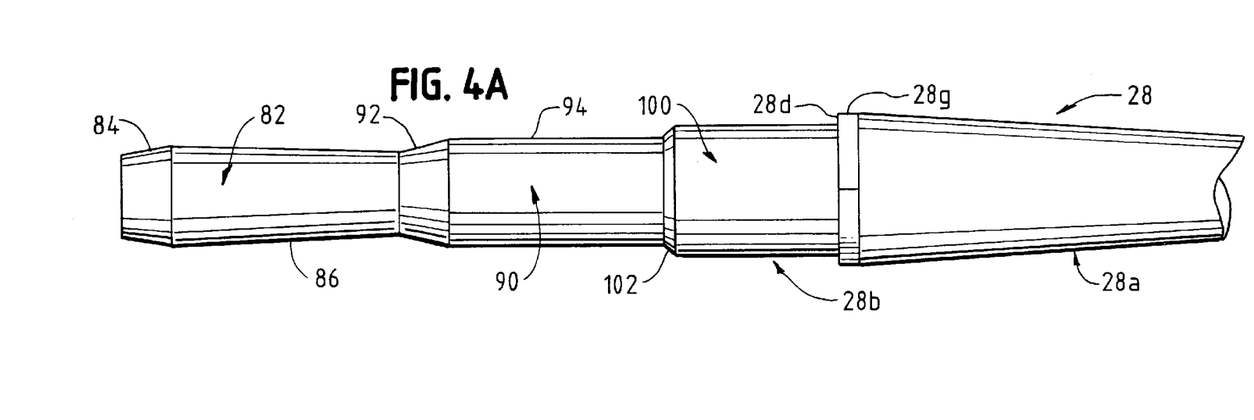
FIG. 4A is an enlarged fragmentary elevational view of a tool taken from FIG. 2.

FIGS. 4, 4A and 5 illustrate details of the attachment of the tool 28 to the body. The tool 30 can be attached in identical fashion and need not be described in detail.

The base part 28b is shown in profile but is understood to be rotationally symmetrical about the central axis A. The base part 28b includes a distal part 82 having a leading tapered surface 84 and a trailing, oppositely tapered surface 86. The term "leading" and "trailing" are referring to the insertion direction D of the base part into the tube 58.

The distal part 82 is formed with an intermediate part 90 having a leading tapered surface 92 and a trailing, substantially level surface 94. The intermediate part 90 is formed with a press fit part 100 having a leading tapered surface 102 and a substantially flat trailing surface 106.

The press fit part 100 is sized to be slightly larger than the inside diameter of the tube 58 to cause a stretching thereof to form a tight, press fit connection between the tool 28 and the tube 58. The leading surface 102 assists in stretching the tube during the press fitting assembly.

As one important aspect of the invention, the tool 28 is adhesively secured to the tube 58. Prior to press fitting the tool 28, adhesive can be applied within the respective open end of the tube 58. The adhesive will thereafter be captured in adhesive trap zones or glue traps 112, 116 when the tool is press fit into the respective open end. Alternately, the adhesive could be pre-positioned within the glue traps 112, 116 before the tool 28 is press fit into the tube. The trap zone 112 is located within an annular depression formed around the base part 28b by the tapered surfaces 86, 92. The adhesive trap zone 116 is formed between the trap zone 112 and the tapered surface 102, around the level surface 94. The glue traps 112, 116 ensure that an adequate amount of adhesive is present between the base part 28b and the tube 58 to make a solid connection.

To assemble the instrument 20, the tube 58 is cut to length. The inside diameter of the tube 58 is reamed to precise tolerance at each end. An outside surface 58b of the tube 58 can be sandblasted to roughen the surface for greater bonding to the body 34, or can be dimpled in two or more places to radially and axially lock the tube to the body 34.

The tube 58 is inserted into a mold, and plastic resin is injected around the tube. After cooling, a quantity ("blob") of adhesive can be placed into the open ends of the tube 58. The tool base parts 28b, 30b can be press fit into the quantity of adhesive, causing adhesive to be trapped within the glue traps 112, 116. Alternately, adhesive (glue) can be applied to the base part 28b and then the base part can be pressed into one end of the tube 58. When a tool is applied to both ends of the tube 58, the press fitting of the base parts 28b, 30b is done one end at a time to allow some entrapped air within the tube 58 to pass through the open end during press fitting at a respective opposite end. The instrument 20, including the adhesive, is then cured at a preselected temperature for a preselected duration. The tool(s) is (are) then typically sharpened before packaging.

FIG. 5 illustrates that the end 58c of the tube 58 is recessed from the end 48a of the body 34 by a distance R, being preferably about 0.015 to 0.02 inches. This relationship allows for the differential thermal expansion between the tube 58 and the body 34 during sterilization.

Adjacent to the tapered surface 28c is a base annular surface 28g. The base annular surface 28g is substantially level.

Because of the recess between the end 58c of the tube 58 and the end 48a of the body 34, the base annular surface 28g remains in close sliding contact with an inside surface 34a. of the body, during relative expansion of the tube 58. This recess or relief dimension "R" avoids the formation of a gap between the shoulder 28d and the end 48a of the body 34 during sterilization when the metal tube 58 would expand at a rate faster then the resin body 34, due to the variation in coefficient of thermal expansion of the two materials. This maintains a seal between the base annular surface 28g and the tube 34 throughout the sliding travel of the end 58c of the tube 58 within the body 34. This prevents any debris from being trapped between the shoulder 28d and the inside surface of the body 34 when the tube 58 subsequently contracts after sterilization.

To accomplish the tight sliding contact between the surface 28g and the inside surface 34a, the surface 28g can have an outer diameter equal to an outer diameter of the tube 58 as shown, that is, the outer diameter of the surface 28g is equal to a diameter of the inside surface 34a. Alternatively, the diameter of the surface 28g can be slightly greater than the tube diameter, and the inside surface 34a. can be slightly stretched to receive the shoulder 28d and the surface 28g.

Figure 6:
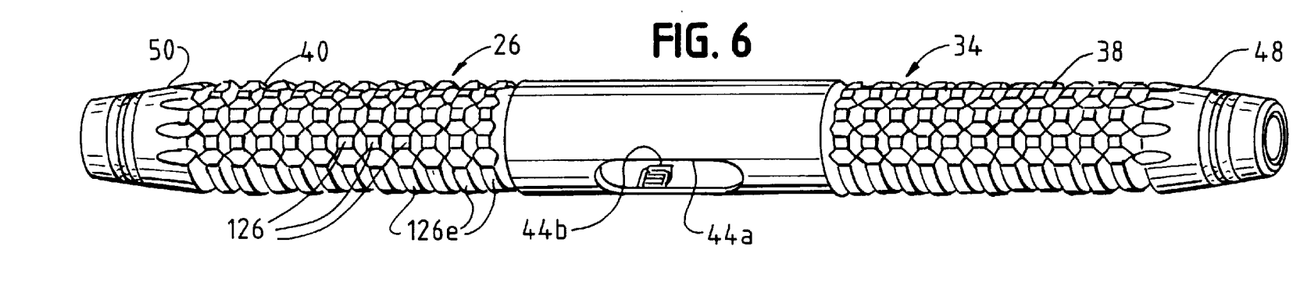
FIG. 6 is a perspective view of a handle portion taken from FIG. 1.
Figure 7:
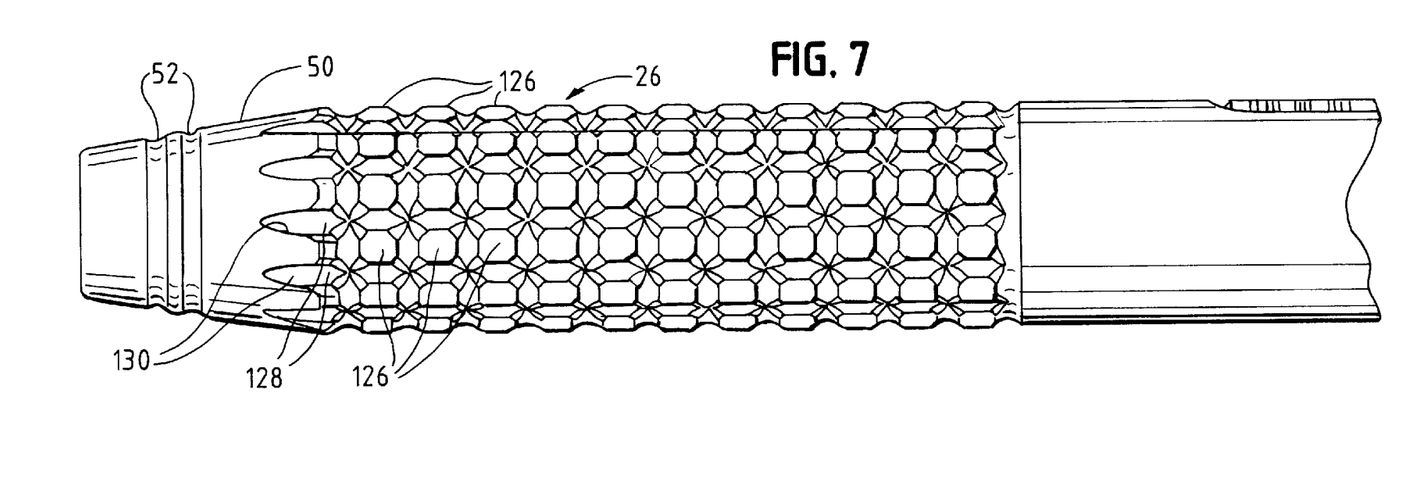
FIG. 7 is an enlarged elevational view of the handle portion shown in FIG. 6.
Figure 8:
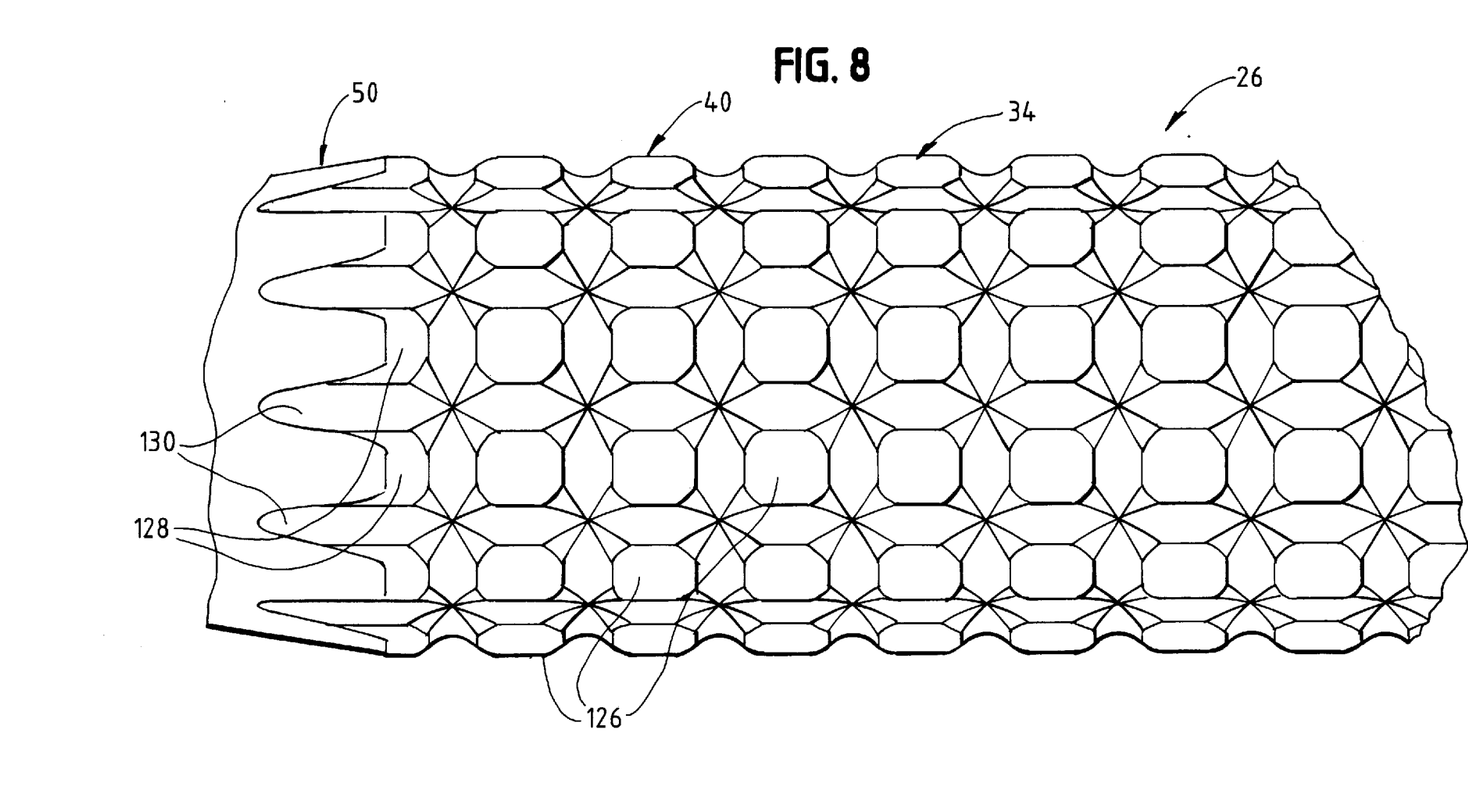
FIG. 8 is a fragmentary enlarged elevational view taken from FIG. 7.

FIGS. 6 through 8 illustrate the handle portion 26 without the installed tools. The contoured regions 38,40 are substantially mirror-image identical. The contoured regions 38, 40 include a plurality of raised domes 126. The domes 126 are arranged in a rectangular grid pattern. At the tapered end portions 48, 50, the domes are tapered to match the contour of the end portions 48, 50, forming ramps 128 separated circumferentially by grooves 130.

As illustrated in FIG. 8, each dome 126 comprises a raised, rounded or dulled, rectangular shape. The rectangular shapes are rounded to prevent the existence of any sharp corners which could theoretically cut a surgical glove worn by a practitioner.

Figure 9:
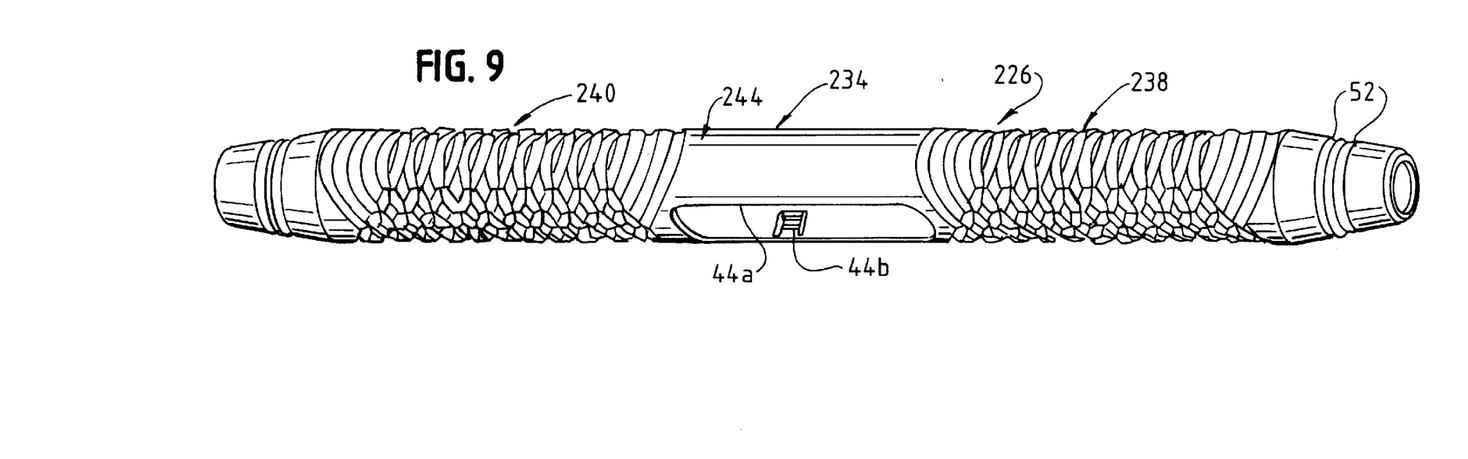
FIG. 9 is a perspective view of an alternate embodiment handle portion of the invention.

FIG. 9 illustrates an alternate handle portion 226. The handle portion 226 is identical to the handle portion 26 except as noted. The handle portion 226 includes a molded plastic body 234 having two contoured regions 238, 240 and a substantially smooth central region 244. The central region 244 includes the recessed area 44a for displaying the raised molded display 44b, such as a trademark. The contoured regions 238, 240 are substantially mirror-image identical.

The contoured regions 238,240 provide effective gripping surfaces for controlled finger manipulation by a user. As demonstrated in FIGS. 10 and 11, the regions 238, 240 provide a different surface pattern when rotated 90°.

Figure 10:
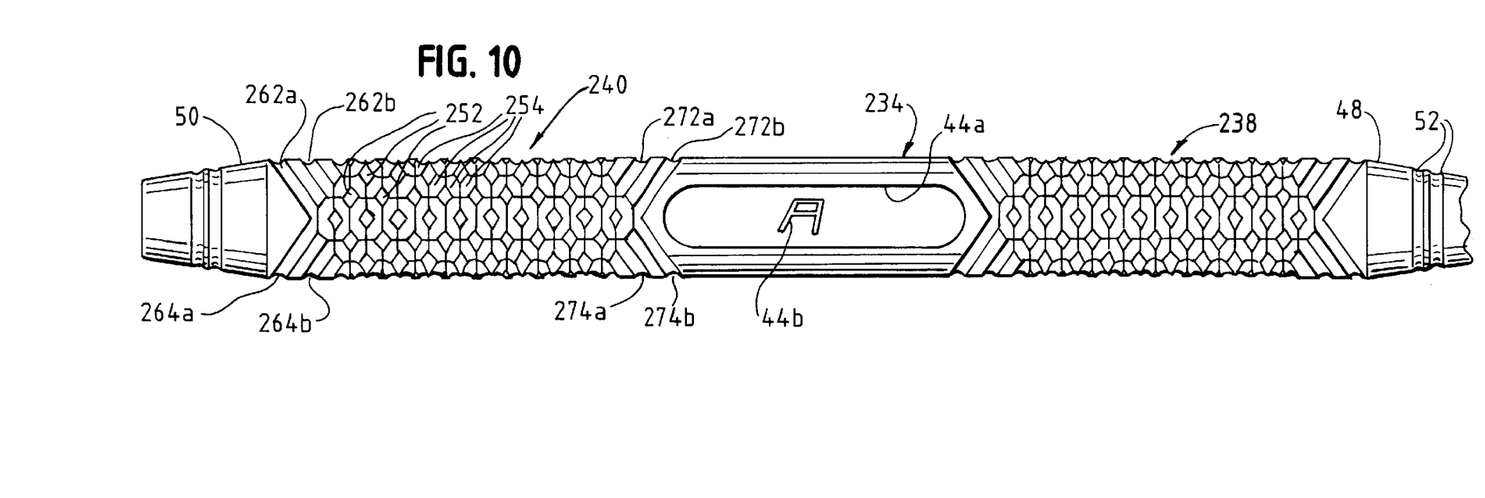
FIG. 10 is a plan view of the handle portion shown in FIG. 9.

In a first orientation, shown in FIG. 10, the pattern includes a plurality of raised diamond shapes 252 surrounded by grooves 254 and arranged in a diagonal grid. The diamond shapes are rounded downwardly or "dulled" to prevent the existence of any sharp corners which could theoretically cut a surgical glove worn by a practitioner.

Adjacent to the end portion 50 are upper arcuate grooves 262a,b and lower arcuate grooves 264a,b. Adjacent to the central region 244 are upper arcuate grooves 272a,b, 274a,b.

Figure 11:
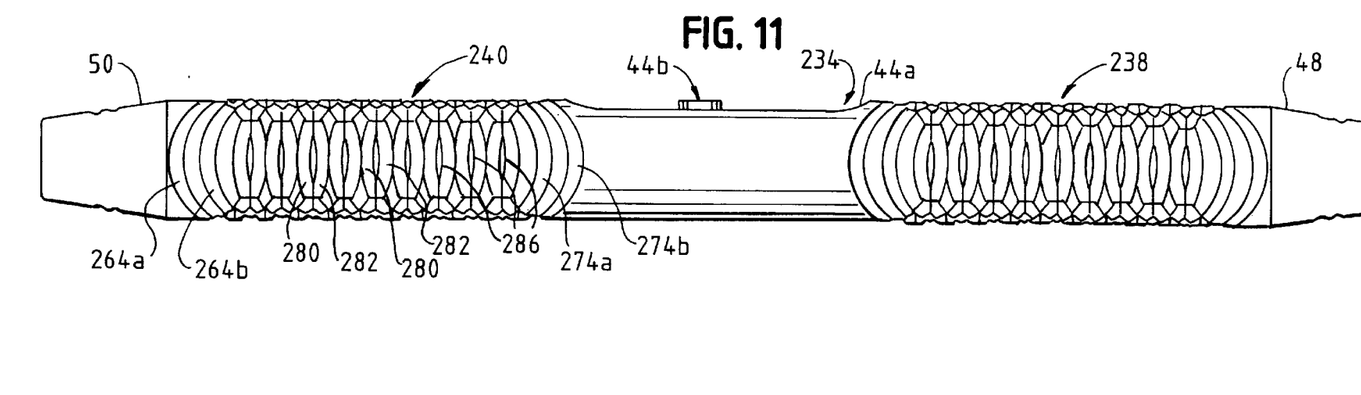
FIG. 11 is a elevational view of the handle portion shown in FIG. 10.
Figure 12:
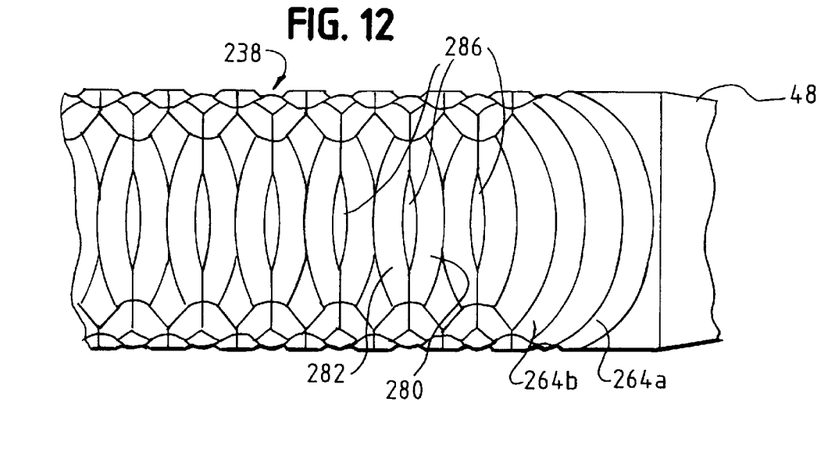
FIG. 12 is a fragmentary enlarged elevational view of the handle portion shown in FIG. 11.

FIGS. 11 and 12 illustrate the contoured regions 238, 240 turned 90° from the view shown in FIG. 10. A plurality of opposing arcuate grooves 280 and opposing arcuate grooves 282 define a plurality of spaced-apart, tapered, ellipse-shaped raised elements 286. Also, this view illustrates a continuation of the arcuate grooves 264a, and 264b, shown in FIG. 10, adjacent the end portion 50, and the arcuate grooves 274a, 274b, adjacent the central region 244.

It should be noted that the contouring shown in FIG. 10 would be visually repeated if the handle was rotated 180°. The contouring shown in FIG. 11 would be visually repeated if the handle was rotated 180°.

One advantage of the molded contoured regions shown in FIG. 1 and FIG. 11, for example, is the fact that the body 34 can be molded easily and effectively using a two part mold. That is, the formations of the contoured surfaces are such that the body can be molded in a mold which can be separated across a single plane to remove the molded body. No side pulls or side separating mold parts are required to remove the molded body. This is accomplished by providing on the sides of the contoured surfaces, a pattern which does not include any undercuts or axial extending recesses which would prevent the lifting of the top mold half from the bottom mold half to remove the body. This is ensured in the embodiment shown in FIG. 1 by the elongated domes 126e which are present at opposite side faces of the body 34.

A parting plane of the mold which was coplanar with the sectional lines 2—2 could be lifted without interfering with contours of the body 34. Regarding the embodiment shown in FIG. 11, the ellipse shaped elements 286 surrounded by the opposing grooves 280, 282 also permit a horizontal parting plane cut through a center of these ellipse shaped elements 286 to be separated vertically to remove the body 234 from the mold.

From the foregoing, it will be observed that numerous variations and modifications may be effected without departing from the spirit and scope of the invention. It is to be understood that no limitation with respect to the specific apparatus illustrated herein is intended or should be inferred. It is, of course, intended to cover by the appended claims all such modifications as fall within the scope of the claims.

What is claimed:

1. An instrument comprising:
   an elongated, metal, reinforcement with a hollow end;
   a handle body molded about the reinforcement;
   a working member which has an affixing stem with first and second abutting, opposing tapers and an attached functional portion, wherein the stem and the tapers slide into the end and wherein the stem is adhesively attached thereto.

2. An instrument as in claim 1, wherein the reinforcement comprises a hollow rod.

3. An instrument as in claim 1, wherein the stem includes at least one glue trap.

4. An instrument as in claim 1, wherein knurlings are molded contemporaneously into the handle.

5. An instrument as in claim 1, wherein the handle has a length parameter which is a predetermined amount greater than the reinforcement.

6. An instrument as in claim 1, wherein the stem carries an attachment cylinder adjacent to one of the tapers.

7. An instrument as in claim 1, wherein a blocking shoulder is formed on the working member and wherein the blocking shoulder is located adjacent to the end.

8. An instrument as in claim 1, wherein the handle has a length on the order of 0.03 inches longer than a length of the reinforcement.

9. An instrument as in claim 1, wherein epoxy adhesive attaches the hollow end of the reinforcement to the stem.

10. An instrument as in claim 1, wherein said stem is press fit into said hollow end.

11. An instrument as in claim 1, wherein said handle body has at least one contoured surface region surrounding a circumference of said handle body, said contoured surface region having different knurling pattern when rotated 90°.

12. An instrument comprising:
    an elongated, metal, reinforcement with a hollow end;
    a handle body molded about the reinforcement;
    a working member which has an affixing stem which slidably engages the hollow end and an attached functional portion wherein the affixing stem includes an exterior periphery which defines two intersecting surfaces each being at a selected angle relative to a central axis of the reinforcement thereby forming a glue trap into which glue in the hollow end flows upon insertion of the stem; and
    wherein said handle body has at least one contoured surface region surrounding a circumference of said handle body, said contoured surface region having different knurling pattern when rotated 90°.

13. The instrument as in claim 12, wherein said contoured knurling surface has a first knurling pattern when viewed from 0° and 180° orientation and a second knurling pattern when viewed at 90° and 270° orientation.

14. An instrument comprising:
    an elongated, metal, reinforcement with a hollow end;
    a handle body molded about the reinforcement;
    a working member which has an affixing stem and an attached functional portion;
    wherein said handle body has at least one contoured surface region surrounding a circumference of said handle body, said contoured surface region having different knurling pattern when rotated 90°;
    wherein said contoured knurling surface has a first knurling pattern when viewed from 0° and 180° orientation and a second knurling pattern when viewed at 90° and 270° orientation; and
    wherein said second knurling pattern includes elongated raised formations and no undercuts to allow a mold parting plane in a two piece mold, to be defined between the 90° and 270° orientation to allow the two piece mold to be opened.

15. The instrument as in claim 14, wherein said second knurling pattern includes a first series of arced grooves facing a first direction and a second series of curved grooves facing a second, opposite direction, said first and second series at least partly superimposed.

16. The instrument as in claim 15, wherein said first knurling pattern includes a plurality of raised diamond shapes arranged in a diagonal grid.

17. The instrument as in claim 14, wherein said first pattern includes a plurality of raised squares arranged in a rectangular grid.

18. The instrument as in claim 17, wherein said second pattern includes a plurality of elongated raised rectangles arranged side by side in a axial direction.

19. The instrument as in claim 14, wherein said second pattern includes a plurality of elongated raised rectangles arranged side by side in a axial direction.

20. A dental instrument comprising:
a handle having an end with an axially oriented opening;
a treatment applying tip with an elongated stem wherein the stem has an exterior periphery which exhibits at least a first tapered region and a second tapered region, wherein the two tapered regions abut one another, wherein the stem extends into and slidably engages a portion of the opening with an interference fit in a first region displaced from the tapered regions.

21. An instrument as in claim 20 wherein the tapered regions form a first adhesive flow path with a different portion of the opening.

22. An instrument as in claim 21 wherein the flow path is substantially filled with an adhesive.

23. An instrument as in claim 21 wherein the stem exhibits a substantially constant diameter second region between the abutting tapered regions and the first region wherein the second region defines a second fluid flow path in conjunction with an adjacent region of the opening wherein the two fluid flow paths are in flow communication.

24. An instrument as in claim 23 wherein the fluid flow paths are substantially filled with adhesive.

25. An instrument as in claim 23 wherein the stem exhibits a shoulder adjacent to an end of the first region, displaced from the second region, wherein the shoulder abuts an annular region of the opening.

26. An instrument as in claim 25 wherein the handle comprises an elongated, hollow metal stem which carries a resin exterior wherein an end surface of the shoulder abuts an end of the hollow metal stem and wherein the first region slidably engages an interior peripheral surface of the hollow metal stem.

27. An instrument as in claim 26 wherein an end of the resin exterior extends past the end of the hollow metal stem and the end surface of the shoulder whereby as the instrument expands in response to sterilization, the end of the hollow metal stem and abutting end surface move relative to the end of the resin though the end of the resin exterior continues to extend past the end of the hollow metal stem and the end surface of the shoulder.

28. A dental instrument comprising:
an elongated metal stem of a first predetermined length at normal use temperature wherein the stem has first and second spaced apart ends wherein a first end has an axially extending opening which terminates at a first end surface;
a resin handle which surrounds the stem and has a second greater length wherein an end portion of the resin handle extends beyond the first end of the stem a predetermined distance;
a treatment member with a treatment end and a stem coupling end wherein the stem coupling end substantially fills the opening for a predetermined distance and wherein a flange of the coupling end abuts the first end surface whereby the flange remains within the end portion of the resin handle notwithstanding expansion of the stem during sterilization.

29. An instrument as in claim 28 wherein the stem coupling end, at least in part, exhibits an adhesive trap in the form of an undulating exterior surface.

30. An instrument as in claim 29 wherein the undulating exterior surface comprises first and second different, abutting tapered sections.

31. An instrument as in claim 30 wherein the abutting tapered sections in combination with a portion of an interior surface of the opening form an adhesive flow path.

* * * * *